United States Patent [19]

Kim

[11] Patent Number: 4,652,668

[45] Date of Patent: Mar. 24, 1987

[54] AROMATIC AMINO ACID DERIVATIVES

[75] Inventor: Sun H. Kim, Chestnut Hill, Mass.

[73] Assignee: Biomeasure, Inc., Hopkinton, Mass.

[21] Appl. No.: 752,386

[22] Filed: Jul. 3, 1985

[51] Int. Cl.$^4$ .......................................... C07C 121/78
[52] U.S. Cl. .................................. 558/390; 558/406; 560/38
[58] Field of Search .................. 558/390, 406; 560/38

[56] References Cited

U.S. PATENT DOCUMENTS 4,344,949  8/1982  Hoefle et al. ..................... 514/307

FOREIGN PATENT DOCUMENTS 0049506  4/1982  European Pat. Off. .

OTHER PUBLICATIONS

Kaltenbronn et al. (1983) Org. Prep. and Proc. Int. 15: 35.
Patchett et al. (1980) Nature 288: 280.

Primary Examiner—Dolph H. Torrence

[57] ABSTRACT

A compound having the formula:

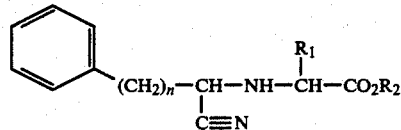

wherein n is 0–5, inclusive; $R_1$ is H or the identifying group of an amino acid; and $R_2$ is H, aralkyl, or alkyl.

6 Claims, 1 Drawing Figure

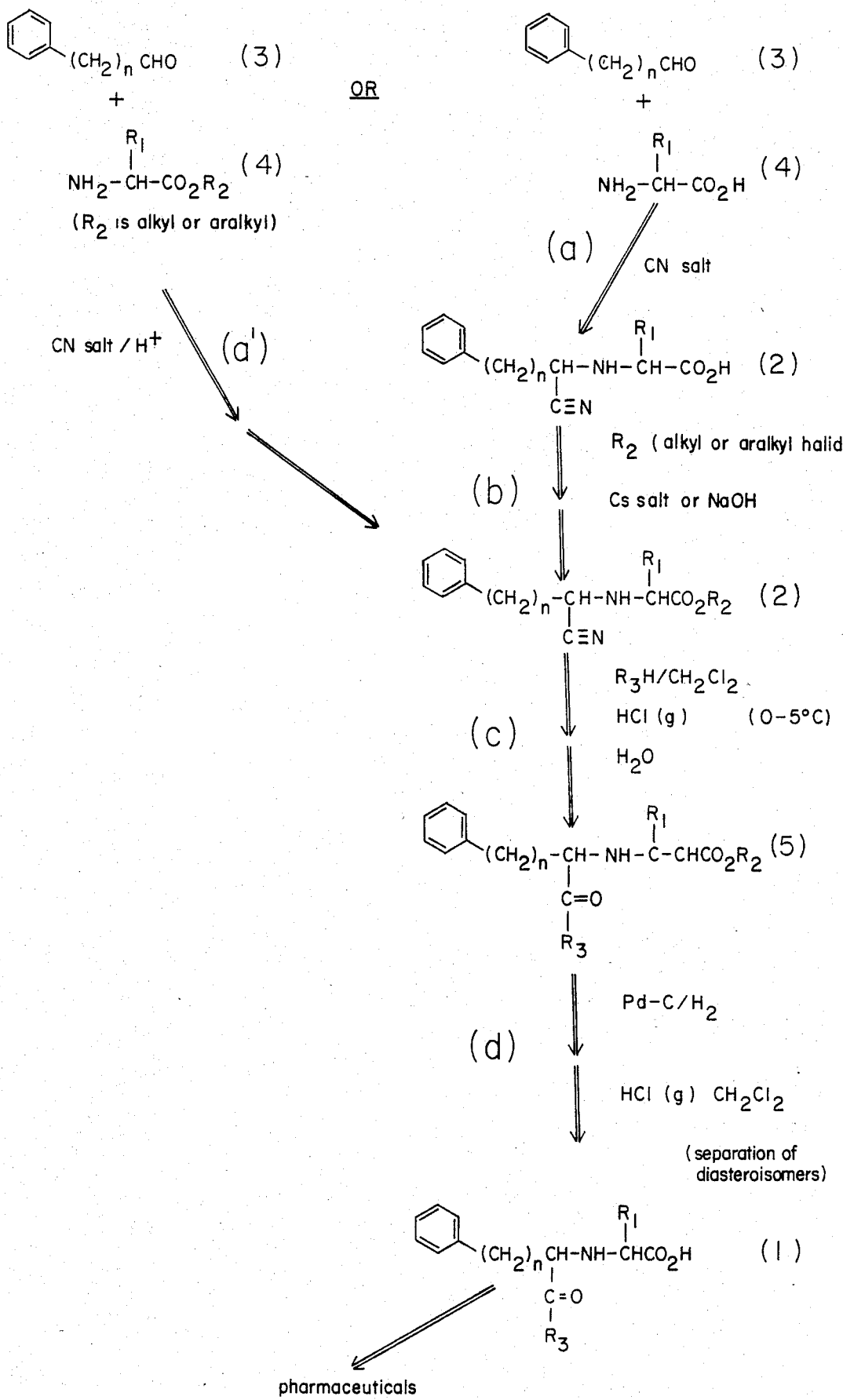

AROMATIC AMINO ACID DERIVATIVES

BACKGROUND OF THE INVENTION

This invention relates to the synthesis of a class of pharmaceuticals of which N-[1-(s)-Ethoxycarbonyl-3-phenylpropyl]-L-alanyl]-L-proline maleate salt (sold under the trade name Enalapril) is representative; such drugs are useful in inhibiting angiotensin converting enzyme in mammals, especially humans.

These pharmaceuticals are commonly synthesized from an intermediate which has the formula

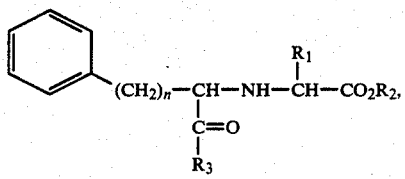

where $R_1$ is an identifying group of an amino acid (D- or L-; e.g., $R_1$ is H in the case of glycine and $CH_3$ in the case of alanine); $R_2$ is H, alkyl (preferably lower (1-5 carbon atoms, inclusive)), or aralkyl, preferably having 6-8 carbon atoms, inclusive (e.g., benzyl); $R_3$ is alkoxy (preferably having 1-5 carbon atoms, inclusive, e.g., ethoxy); and n is 0-5, inclusive, most preferably 0-2, inclusive.

SUMMARY OF THE INVENTION

In general, the invention features a method of making compound (1) using methods and materials which are considerably less costly than prior art methods and materials. The new synthetic method involves a key intermediate, which is a new compound of the present invention. This new compound has the formula:

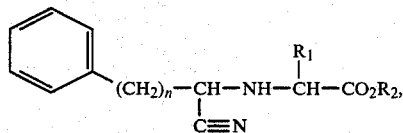

(2)

where $R_1$, $R_2$, and n are as defined above.

Compound (2) is synthesized by reacting together, in the presence of alkali cyanide, two readily available compounds:

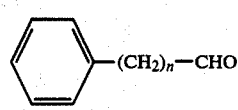

(3)

and

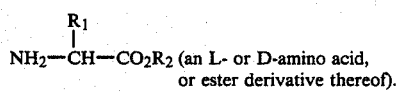

(4)

$NH_2-CH-CO_2R_2$ (an L- or D-amino acid, or ester derivative thereof).

DESCRIPTION OF THE PREFERRED EMBODIMENTS

The drawing is first described.

Drawing

The FIGURE is a flowchart illustrating the steps in synthesizing compounds of the invention.

STRUCTURE

The new compounds (2) have the structure recited in the Summary of the Invention, above. New compounds (5) have the structure shown in the flowchart.

Synthesis

The compounds of formula (2) include compounds in which $R_2$ is H; i.e., the compound is a carboxylic acid; and compounds in which $R_2$ is an alkyl or aralkyl group; i.e., the compound is an ester. Generally, it is preferred that an ester be formed, so that the formula (2) compounds which are acids are intermediates in the synthesis of formula (2) compounds which are esters. The ester group desirably protects the compound during the subsequent reactions (described below) which result in the formation of the compound of formula (1).

As shown in the flowchart of the FIGURE, the ester group can be attached either by employing in the condensation reaction, in place of an amino acid, an $R_2$-substituted ester derivative of an amino acid (step ($a^1$) in the FIGURE). Alternatively, and more preferably, esterification is carried out after the condensation reaction (step (b) in the FIGURE).

The condensation reaction is preferably carried out at room temperature in an inert polar solvent, e.g., water, an alcohol, e.g., ethoxyethanol; tetrahydrofuran; acetonitrile; or a mixture of such solvents, in the presence of alkali-cyanide, e.g., NaCN or KCN. These reagents are commercially available and inexpensive.

Esterification is carried out by any suitable conventional method, e.g., acid catalyzed esterification, or use of an organic or inorganic salt (e.g., tertiary alkylammonium, sodium, potassium, or cesium salt) in conjunction with an alkyl or aralkyl halide (e.g., as described in Tetrahedron Letters (1980) 36, 2409).

As mentioned above, the compounds of formula (2) are key intermediates in the production of compounds of formula (1), which are used to make pharmaceuticals. The general reaction scheme by which compounds (2) are used to make compounds (1) is shown in the flowchart of the FIGURE.

Compound (2) is esterified at the C≡N group (step (c) in the FIGURE) to form new compound (5) of the invention. This is carried out in a two-step process, the first step of which involves reacting the compound of formula (2) with an alcohol ($R_3OH$) and dry HCl in an inert polar solvent such as $CH_2Cl_2$ or chloroform; this reaction is generally known as a Pinner Synthesis; Zilberman et al. (1962) Russ. Chem. 31, 615. The reaction is carried out at between $-15°$ C. and room temperature to avoid side reactions. The reaction results in the formation of an iminoester hydrochloride salt:

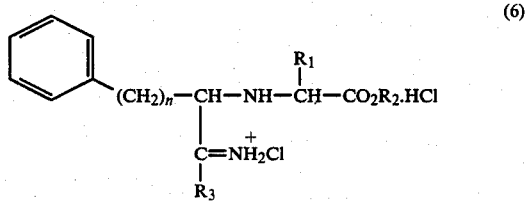

(6)

Crude compound (6) (not shown in the FIGURE) is then partially hydrolyzed with water at room temperature to form ester (5).

Step (d) is then carried out, by which the $R_2$ group is catalytically replaced by H to form compound (1), which is then used to form pharmaceuticals according to well-known prior art methods (e.g., Kaltenbronn et al. (1983) Org. Prep. & Proc. Int. 15, 35; Patchett et al. (1980) Nature 288, 280; European Pat. No. 49,506 (1981)). Isolation and purification of compound (1) is carried out by standard techniques, e.g., column chromatography or crystallization.

Specific compounds are made as follows.

N-(1-Cyano-3-Phenylpropyl)-L-Alanine

L-alanine (3.56 g) is dissolved in aqueous sodium cyanide (1.96 g/40 ml) and a methanolic solution of 3-phenylpropionaldehyde (5.63 g/25 ml) is added under vigorous stirring, bringing the total volume to 65 ml. The mixture is stirred at room temperature for 3 hours, extracted with chloroform, and acidified with 2NHCl (pH 3-4). The resulting precipitate is collected, washed, and dried, and used in the next reaction without further purification [m.p.=115° C. (decompose); TLC (Silica gel; $CHCl_3$/MeOH/HOAC=9:1:0.5); Rf=0.60].

N-(1-Ethoxycarbonyl-3-Phenylpropyl)-L-Alanine Benzylester

Cesium carbonate (4.23 g) and benzylbromide (2.22 g) are added to a suspension of N-(1-cyano-3-phenylpropyl)-L-alanine (3.02 g) in 30 ml dry dimethylformamide. The resulting mixture is stirred 8-12 hours at room temperature and, after evaporation of solvent, partitioned between water and chloroform. The chloroform layer is dried over $MgSO_4$ and the solvent removed to yield 4.24 g of a pale yellow oil, N-(1-Cyano-3-Phenylpropyl)-L-Alanine Benzylester [TLC (Silica gel; $CHCl_3$/Acetone=9:1); Rf=0.65]. Aqueous sodium hydroxide in dimethyl sulfoxide can be used in place of cesium salt in dimethyl formamide.

N-(1-Cyano-3-Phenylpropyl)-L-Alanine Benzylester (4.24 g) is then dissolved in 65 ml dry dichloromethane and diluted with 2.39 g absolute ethanol. After cooling on ice, the solution is saturated with dry HCl, stored for 2 days at 0°-5° C., and evaporated to form a residue which is dissolved in 30 ml of a 2:1 acetonitrile:water mixture at room temperature for 15 minutes. An excess of aqueous $NaHCO_3$ is then added to the mixture, which is extracted with chloroform several times, dried over $MgSO_4$, and placed under vacuum to evaporate the solvent, yielding N-(1-Ethoxycarbonyl-3-Phenylpropyl)-L-Alanine Benzylester [TLC (Silica gel; $CHCl_3$/acetone=9:1); Rf=0.60].

[R and S]-N-(1-Ethoxycarbonyl-3-Phenylpropyl)-L-Alanine

N-(1-Ethoxycarbonyl-3-Phenylpropyl)-L-Alanine Benzylester (4.2 g) is dissolved in 40 ml ethanol, to which is added 630 mg 10% Pd-C and a few drops of acetic acid. Hydrogenation occurs under a 30 psi hydrogen atmosphere at room temperature overnight. The resulting mixture is filtered through celite and dried under vacuum to remove the solvent, yielding a residue. The residue is partitioned between chloroform and aqueous 5% $NaHCO_3$, separated, and the chloroform layer further washed with aqueous 5% $NaHCO_3$. The aqueous layers are combined, acidified to pH 3.5 with dilute HCl, extracted with chloroform or ethylacetate several times, dried over $MgSO_4$, and placed under vacuum to evaporate the solvent and yield 2.5 g of the diastereoisomeric product, a brown sticky solid [TLC (Silica gel; $CHCl_3$/MeOH/HOAC=9:1:0.5); Rf=0.4].

Separation of Diastereoisomers

N-(1-(r)-Ethoxycarbonyl-3-phenylpropyl)-L-alanine

A solution of crude [r and s] N-(1-Ethoxycarbonyl-3-Phenylpropyl)-1-Alanine (2.5 g) in dry methylene chloride (2.5 ml) is saturated with dry HCl gas. The mixture is stirred at room temperature for 3 hours and the precipitate is collected by filtration, washed with a small amount of methylene chloride, and dried to yield 1.2 g of a colorless solid [m.p. 193°-195° C.; $[\alpha]_D = -27.4°$ (C=0.98, MeOH)].

N-(1-(s)-Ethoxycarbonyl-3-Phenylpropyl)-L-Alanine

The above filtrate is evaporated in vacuo to give 1.4 g of brown hygroscopic solid which is used for the next reaction without further purification.

N-(1-(s)-Ethoxycarbonyl-3-Phenylpropyl)-L-Alanyl-Proline-Benzylester

To an ice-cooled solution of L-proline benzylester hydrochloride (0.58 g) and crude N-(1-(s)-Ethoxycarbonyl-3-Phenylpropyl)-L-Alanine Hydrochloride (0.73 g) in $DMF/CH_2Cl_2$ (1:1, 20 ml) is added N-methylmorpholine (0.53 g), followed by 1-hydroxybenzotriazole (0.38 g). After 15 min of stirring, a cold solution of dicyclohexylcarbodiimide (0.65 g) in dry methylenedichloride (6 ml) is added and the mixture stirred at 0°-5° C. for 1 hour, then allowed to cool at room temperature overnight. The mixture is filtered and the filtrate after washing with aqueous $NaHCO_3$ concentrated in vacuo to dryness to give 1.35 g of yellow viscous oil [TLC (Silica gel; $CHCl_3$/acetone=9:1); Rf=0.4]. The crude product is used for next reaction without further purification.

N-(1-(s)-Ethoxycarbonyl-3-Phenylpropyl-L-Alanyl-L-Proline Maleate salt (sold as MK-421 or Enalapril)

To a mixture of crude N-(1-(s)-Ethoxycarbonyl-3-Phenylpropyl)-L-Alanyl-L-Proline Benzylester (1.35 g) is added 10% Pd-c (0.2 g) in ethanol (20 ml) containing a few drops of acetic acid, and the mixture hydrogenated under a 30 psi hydrogen atmosphere overnight. The mixture is filtered through a celite pad, washed with methanol, and the filtrate is concentrated in vacuo to dryness. The residue is dissolved in 10 ml acetonitrile and maleic acid (0.32 g) is added with warming until a clear solution is obtained. After overnight standing, colorless crystals are collected by filtration, washed with small amount of acetonitrile, and then dried [0.58 g; m.p. 143°-144° C.; $[\alpha]_D^{20} = -40.2°$ (C=1.0, MeOH)].

Other embodiments are within the following claims.

I claim:

1. A compound having the formula:

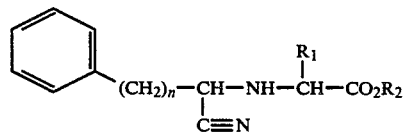

wherein n is 0-5, inclusive; $R_1$ is H or the identifying group of an amino acid; and $R_2$ is H, aralkyl, or alkyl.

2. The compound of claim 1 wherein $R_2$ is alkyl having 1-5 carbon atoms, inclusive.

3. The compound of claim 1 wherein $R_2$ is aralkyl having 6-8 carbon atoms, inclusive.

4. The compound of claim 1 wherein n is 2, $R_1$ is $CH_3$, and $R_2$ is H.

5. The compound of claim 1 wherein n is 2, $R_1$ is $CH_3$, and $R_2$ is benzyl.

6. A method of making a compound of the formula:

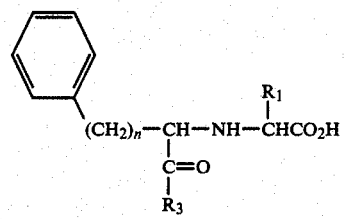

wherein n is 0-5, inclusive; $R_1$ is H or the identifying group of an amino acid; $R_2$ is H, aralkyl, or alkyl; and $R_3$ is alkoxy, said method comprising the steps of (a) reacting together a compound of the formula

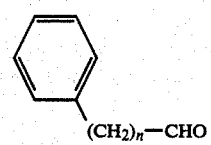

and a compound of the formula

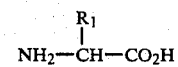

to form a condensation product of the formula:

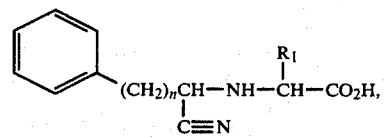

(b) reacting said condensation product with a compound containing said $R_2$, under conditions which cause the formation of the ester product of the formula:

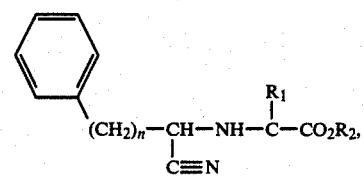

(c) reacting said ester product with a compound containing said $R_3$, under conditions which cause the formation of a diester product of the formula:

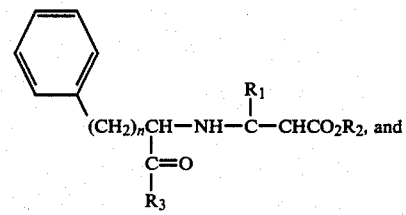

(d) catalytically treating said diester product to remove said $R_2$ to form said compound of the formula:

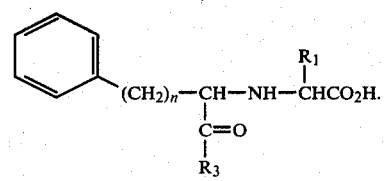

* * * * *